United States Patent [19]

Saito et al.

[11] 4,195,101

[45] Mar. 25, 1980

[54] 2',6'-DIHYDROXY-9-(2,5-DIHYDROXY-PHENYL)OCTYLPHENONE AND ITS USE AS AN ANTI-OXIDANT

[75] Inventors: Yutaka Saito, Funabashi; Yukichi Kimura, Narashino; Tomonori Sakamoto, Chiba; Masafu Shinbo; Shoji Kameyama, both of Odawara, all of Japan

[73] Assignee: The Lion Dentifrice Co. Ltd., Tokyo, Japan

[21] Appl. No.: 946,968

[22] Filed: Sep. 29, 1978

[30] Foreign Application Priority Data

Nov. 22, 1977 [JP] Japan .................................. 52-140372
Aug. 22, 1978 [JP] Japan .................................. 53-102044

[51] Int. Cl.² .............................................. A23L 1/28
[52] U.S. Cl. .................................... 426/546; 252/404; 260/590 D; 260/592; 426/655

[58] Field of Search ............... 426/542, 544, 545, 546, 426/654, 655; 260/592, 398.5, 590 D; 252/398, 404, 397

[56] References Cited

U.S. PATENT DOCUMENTS

| 3,732,111 | 5/1973 | Berner et al. ......................... 426/542 |
| 4,110,483 | 8/1978 | Bishov .............................. 426/655 X |

OTHER PUBLICATIONS

Chipault et al., "The Antioxidant Properties of Natural Spices," *Food Research*, vol. 17, 1952.
Braverman, *Introduction to the Biochemistry of foods*, 1963.
*Fenaroli's Handbook of Flavor Ingredients*, The Chemical Rubber Co., 1971.

*Primary Examiner*—Arthur L. Corbin
*Attorney, Agent, or Firm*—Toren, McGeady and Stanger

[57] ABSTRACT

Oxidation of foodstuff is prevented by admixing with the foodstuff 2',6'-dihydroxy-9-(2,5-dihydroxyphenyl)-octylphenone.

3 Claims, 3 Drawing Figures

2',6'-DIHYDROXY-9-(2,5-DIHYDROXYPHENYL-)OCTYLPHENONE AND ITS USE AS AN ANTI-OXIDANT

BACKGROUND OF THE INVENTION

The present invention relates to a novel compound 2',6'-dihydroxy-9-(2,5-dihydroxyphenyl)octylphenone and its use as an anti-oxidant.

Synthetic anti-oxidants for foodstuffs are known, such as dibutylhydroxytoluene (BHT for brevity) and butylhydroxyanisole (BHA for brevity). These compounds are, however, disadvantageous in that their amounts to be added to foodstuffs should be strictly controlled. For example, a maximum permissible content of BHT or BHA in fats and oils or in butter under the Japanese safety regulations must not exceed 0.02%, such limitation bringing about an insufficient anti-oxidative effect in some cases.

Besides the above named anti-oxidants for foodstuffs, several compounds have recently been proposed, for example α,ω-bis(2,5-dihydroxyphenyl)alkanes having the structural formula

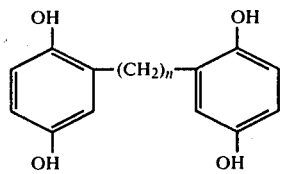

(as disclosed in Japanese Patent Publication No. 42-6973), and hexahydrocurcumin or octahydrocurcumin (as disclosed in Japanese Patent Publication No. 48-39930). The compounds, however, have drawbacks in their synthesis and effectiveness. It is a recent trend that anti-oxidants originating in natural products are preferred to synthetic anti-oxidants as food additives from the standpoint of safety and taste. Unfortunately, however, very few natural anti-oxidants are known which can compare with synthetic ones in anti-oxidative activities, and it has been eagerly desired to develop highly anti-oxidative natural anti-oxidants.

SUMMARY OF THE INVENTION

It is therefore an object of the present invention to provide novel anti-oxidants for foodstuffs which compare favorably with synthetic anti-oxidants in anti-oxidative activities and which are free from the problems of safety and taste.

The compound proposed in the present invention is 2',6'-dihydroxy-9-(2,5-dihydroxyphenyl)octylphenone, which serves as a powerful anti-oxidant for foodstuffs, and has not hitherto been known or described in literature.

The present invention has been completed by the discovery that the extraction and separation of mace, or Myristica fragrans Hautt, which is a known spice, successively with petroleum ether, diethylether, n-hexane and carbon tetrachloride, followed by column chromatographic separation, can produce the compound 2',6'-dihydroxy-9-(2,5-dihydroxyphenyl)octylphenone which is very effective as an anti-oxidant in foodstuffs, such as lard or the like, exhibiting much higher anti-oxidative activities than the conventional anti-oxidant BHA.

DETAILED DESCRIPTION OF THE PREFERRED EMBODIMENTS

The compound 2',6'-dihydroxy-9-(2,5-dihydroxyphenyl)-octylphenone is a compound having the following structural formula.

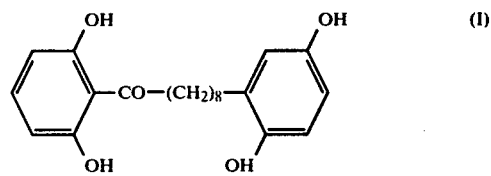

This compound is obtained as needle-like or plate-like crystals white to pale-yellow in appearance, tasteless, odorless and non-irritative, and has a melting point of 123.5° to 124° C. The compound is soluble in various solvents as shown in Table I. In Table I, the solubility of the compound was rated by A, B, C and D and each rating was determined for 10 mg of the crystal as follows.

A: Soluble in less than 0.1 ml of solvent.
B: Soluble in 0.1–1.0 ml of solvent.
C: Soluble in 1.0–10.0 ml of solvent.
C: Soluble in more than 10.0 ml of solvent.

Table I

| | Rating of Solubility | |
|---|---|---|
| Solvent | at 25° C. | at the boiling point of solvent |
| Petroleum ether | D | D |
| Ligroin | D | D |
| n-Hexane | D | D |
| Cyclohexane | D | D |
| Carbon tetrachloride | D | C |
| Chloroform | C | C |
| Dichloromethane | D | C |
| 1,2-Dichloroethane | C | A |
| Toluene | D | B |
| Benzene | D | B |
| Diethylether | A | A |
| Ethyl acetate | A | A |
| Acetone | A | A |
| Methyl alcohol | A | A |
| Ethyl alcohol | A | A |
| n-Propyl alcohol | A | A |
| iso-Propyl alcohol | A | A |
| n-Butyl alcohol | A | A |
| Acetonitrile | A | A |
| Pyridine | A | A |
| Carbon disulfide | D | D |
| Water | D | D |

Figure 1:
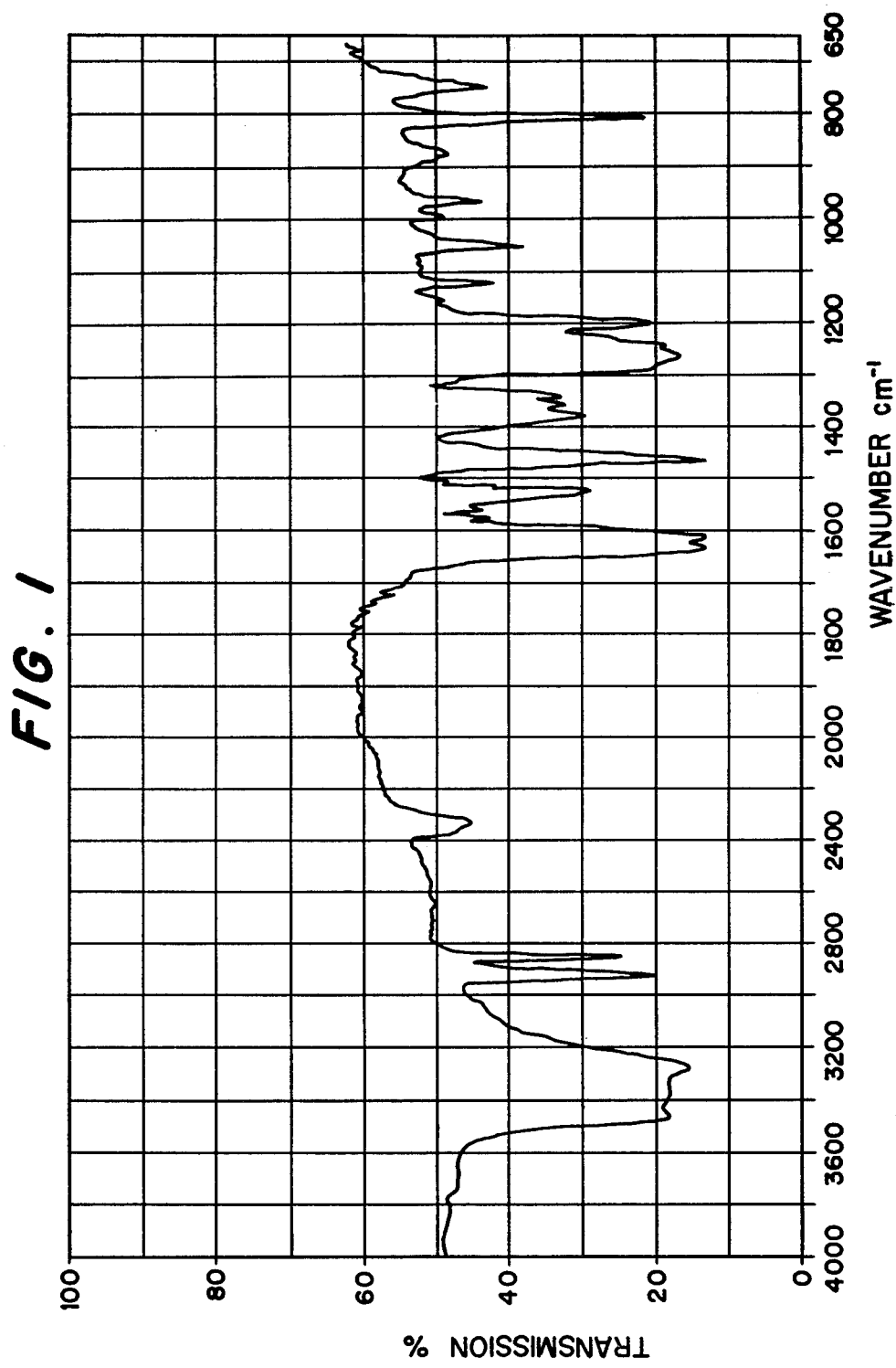
FIG. 1 is an infrared absorption spectrum of the compound of the present invention taken in KBr disc.

The infrared absorption spectrum of the compound of the present invention is shown in FIG. 1.

The compound may be obtained by the following method. Mace, a dried arillode of nutmeg, is subjected to extraction with petroleum ether to leave a residue, which is further subjected to extraction with diethylether. The diethylether is removed by distillation from the extract, while the residue, after added with carbon tetrachloride, is heated under reflux and centrifugally separated to give an insoluble matter. The insoluble matter is then subjected to column chromatographic separation with silica gel as the adsorbent and a mixed chloroform-acetone (9:1) solvent and acetone as the eluants. The eluted fractions which exhibit anti-oxidative activities, are subjected again to column chromatographic separation with silica gel as the adsorbent and a mixed chloroform-acetone-n-hexane (8:1:1) solvent as the eluant to produce fractions exhibiting anti-oxidative activities. The fractions thus produced are mixed with acetone and n-hexane and subjected to extraction. The resulting solution in n-hexane and acetone is chilled and the precipitated crystalline material is recrystallized from benzene, resulting in obtaining the compound expressed by the structural formula (I) above.

The solvents to be used in the extraction and washing of the compound are not limited to those named above, but include those mentioned in Table I. For example, those in which the compound is readily soluble, such as ethyl acetate and ethyl alcohol, may be used for extraction and those in which the compound is insoluble or hardly soluble, such as ligroin and chloroform may be used for washing.

Alternatively, the compound can be separated from mace by virtue of differences in its solubility in some solvents depending on temperature. That is to say, for example, 1,2-dichloroethane, toluene or benzene in which the compound is insoluble or hardly soluble at room temperature is used for the extraction of the compound direct from made in heated conditions, the extract being chilled to precipitate the compound and the precipitate being purified by chromatography or other means.

The compound of the present invention is useful as an anti-oxidant in order to prevent foodstuffs from oxidative denaturation. The anti-oxidative activities of the compound is so strong that the oxidative denaturation of lard can be effectively prevented by adding as small as 0.005% by weight of the compound, to the same extent as done by adding 0.02% by weight of BHA. When the amount of the compound added is increased to 0.02% by weight, it brings about anti-oxidative effect approximately twice as high as the same amount of BHA. This is indicative that sufficient anti-oxidative effects can be obtained by the compound of the present invention in a very small amount.

Different from most of the synthetic anti-oxidants, the compound of the present invention, which is obtained by extraction and separation from a natural product, has no problem in safety with an $LD_{50}$ value of more than 2,000 mg/kg of mouse by oral administration. The $LD_{50}$ value of the compound is about the same as in BHT, and much better than 1,100 mg/kg of mouse in BHA.

The effective amount of the compound of the present invention is usually between 0.001 and 0.1% by weight in lard and other foodstuffs. However, any larger amount brings about no problems since the compound is tasteless, odorless, almost colorless and non-irritative. The compound may also be useful as an additive to various organic materials, including plastics, rubbers, pharmaceuticals, cosmetics, paper and the like.

The procedure for the preparation of 2',6'-dihydroxy-9-(2,5-dihydroxyphenyl)octylphenone is as follows.

Figure 2:
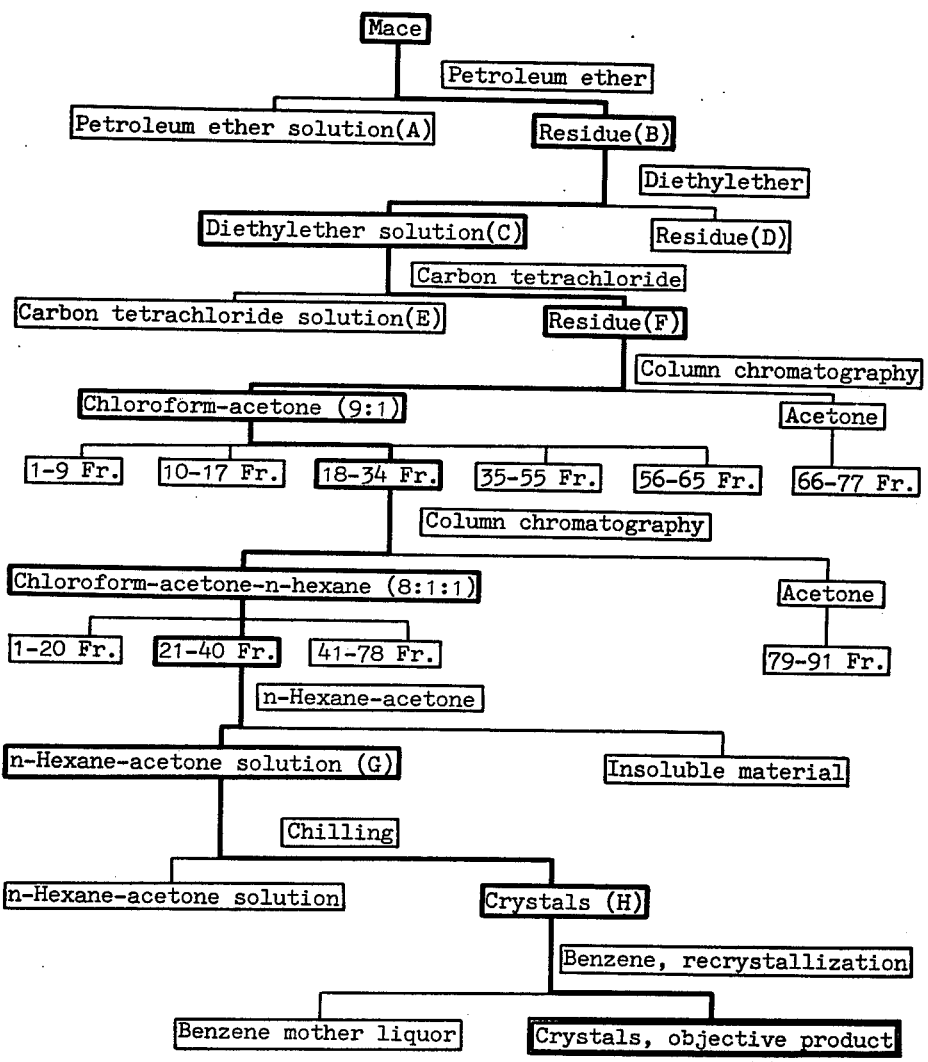
FIG. 2 is a flow diagram of the procedure for the preparation of the compound of the invention.

The preparation procedure of 2',6'-dihydroxy-9-(2,5-dihydroxyphenyl)octylphenone from mace is outlined by a flow diagram in FIG. 2.

Pulverized mace having an about 10-mesh particle size and weighing 1,000 g was immersed in 1500 ml of petroleum ether and, after standing at room temperature for 24 hours, filtered and separated to form a petroleum ether extract (A) and a residue (B). The residue (B) was air-dried, further pulverized so as to pass a 24-mesh screen and added with 1,500 ml of diethylether and, after standing at 5° C. for 24 hours, the mixture was filtered to form a diethylether extract (C) and a residue (D). The same extraction procedure was repeated twice for the residue (D) and the resultant diethylether extract was altogether subjected to distillation under reduced pressure to completely remove the solvent. The residue remaining was dispersed in 150 ml of carbon tetrachloride and, after heating under reflux for 30 minutes with agitation followed by cooling to room temperature, separated centrifugally at 10,000 r.p.m. for 30 minutes to form a solution in carbon tetrachloride (E) and an insoluble matter (F). The insoluble matter (F) was further washed twice with portions of carbon tetrachloride in the same manner as above to finally produce an insoluble matter (F) weighing 4.10 g. This insoluble matter (F) was then dissolved in 10 ml of a mixed chloroform-acetone (9:1) solvent and subjected to column chromatographic separation under the following conditions to form 77 fractions.

Adsorbent: Silica gel (Wakogel C 200, product of Wako Junyaku Co., Japan)
Column: 32.0 cm long and 3.0 cm in inner diameter
Eluants: Chloroform-acetone (9:1) mixture and acetone
Velocity of elution: 20 g/18 minutes
Fraction size: 20 g/fraction Of the 77 fractions thus formed, the 18th to 34th fractions exhibited anti-oxidative activities, containing 1.58 g of the eluted product as dried.

The eluted product contained in the 17 fractions (18th to 34th fraction) thus collected was altogether subjected to the second column chromatographic separation under the following conditions to form 91 fractions.

Adsorbent: Same as in the first chromatographic separation
Column: Same as in the first chromatographic separation
Eluants: Chloroform-acetone-n-hexane (8:1:1) mixture and acetone
Velocity of elution: 20 g/31 minutes for the 1st to 24th fractions and 20 g/11 minutes for the 25th to 78th fractions
Fraction size: 20 g/fraction Of the above 91 fractions, the 21st to 40th fractions containing 1.20 g of the product as dried were collected.

The eluted product contained in the 21st to 40th fractions was dried and again dissolved in a small amount of acetone. The resulting solution was, after mixing with about 10 ml of n-hexane, heated on a water bath at 75° C. to produce solution in a mixed solvent of n-hexane and acetone (G) with the insoluble matter to be removed. This procedure was repeated, and the resultant solution was altogether chilled to 5° C. where a precipitated crystalline material (H) was taken and recrystallized using benzene, to form 0.46 g of a final product (I), which was identified to be the objective 2',6'-dihydroxy-9-(2,5-dihydroxyphenyl)octylphenone, having the following properties.

Appearance: Pale-yellow, needle-like crystals
Results of elementary analysis (as $C_{21}H_{26}O_5$):

Calculated: C, 70.37%; H; 7.31%; Found: C, 70.61%; H; 7.23%.

Infrared absorption bands in KBr disc, cm$^{-1}$ (cf. FIG. 1):
3600–3200
1625
1200

Figure 3:
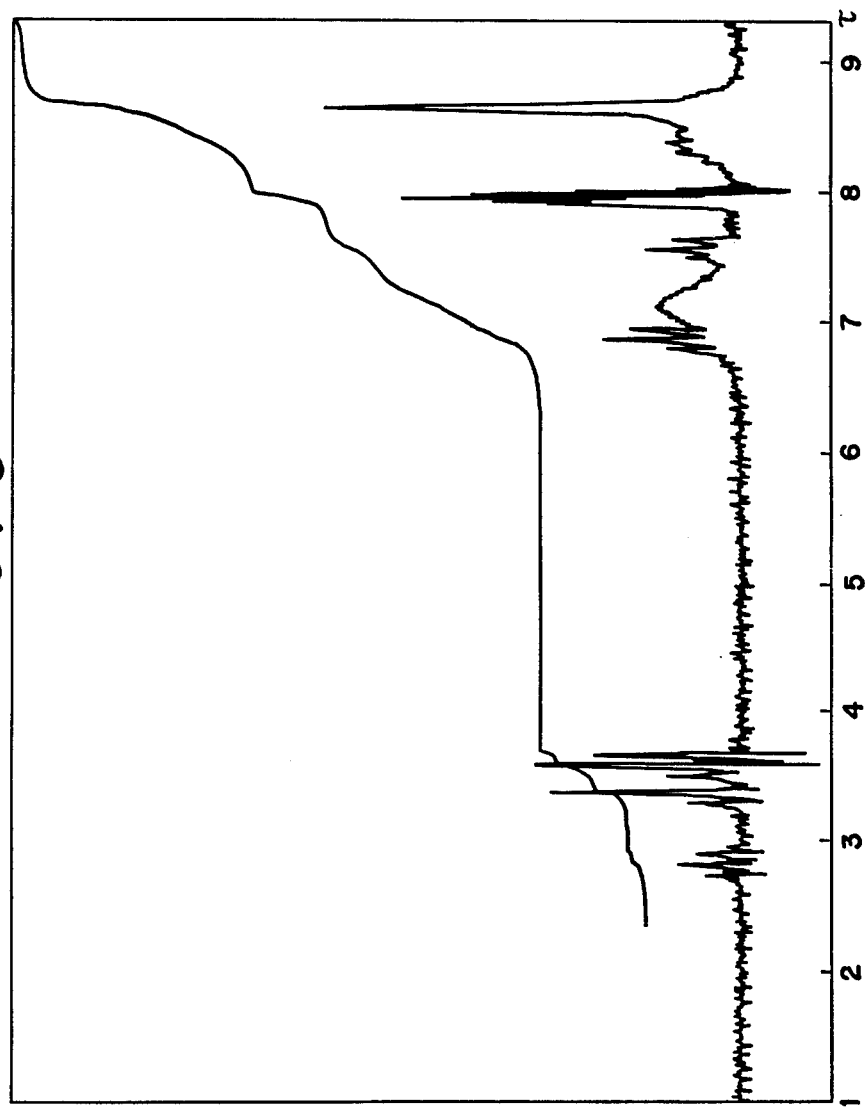
FIG. 3 is a nuclear magnetic resonance spectrum of the compound of the invention taken in deuterated acetone.

NMR spectrum in deuterated acetone, TMS, $\pi$ (cf. FIG. 3):
2.82 (1H, triplet)
3.25 (3H, multiplet)
3.60 (2H, doublet)
6.88 (2H, triplet)
7.56 (2H, triplet)
8.50 (14H, multiplet)

Mass spectrometry:
M+358 (molecular weight as $C_{21}H_{26}O_5$ 358.193)

The above-obtained compound was tested for its anti-oxidative effects in terms of peroxide value by the active oxygen method (AOM) and also in terms of oxygen absorption. As a result, it was demonstrated that the compound has excellent anti-oxidative activities and can be useful as an effective anti-oxidant in foodstuffs and other organic materials. Each of the tests I and II are described below together with the results thereof.

TEST I.

Varied amounts of the compound were admixed with and uniformly dissolved in portions of refined lard each weighing 20 g to prepare test samples. Each test sample was kept in an oil bath of thermostat at 97.5°±0.5° C., while air was forcedly blown into the lard at a rate of 0.23 ml/hour.

The thus treated samples of the lard were analyzed for the peroxide value (POV for brevity) periodically or at certain intervals, in accordance with the modified Lea's method as described in "Yukagaku" (Journal of Japan Oil Chemist Society), vol. 19(15), p. 340, 1970. The results are shown in Table II.

In comparison, similar experiments were undertaken for the samples of the same lard with addition of BHA instead of the compound of the present invention or without addition of any anti-oxidant. The results are also shown in Table II.

Test II.

The compound of the present invention was determined for the rate of oxygen absorption in a corn salad oil to which 0.02% by weight of the compound had been added. For the purpose, 2 grams of the corn salad oil sample was taken in the receptacle of Warburg's manometer with thermostat at 60°±0.1° C., which was shaken with 110 vibrations per minute in a vibration amplitude of 60 mm. The rate of oxygen absorption was determined by reading the manometer according to the procedure set forth in "Jikken Kagaku Koza" (Lectures in Experimental Chemistry), vol. 24, p. 85, 1958, Maruzen Publishing, Japan. In this testing, the receptacle was totally wrapped with an aluminum foil to prevent the photooxidation of the oil, and mercury was used as the manometer fluid in place of Brodie's solution in order to minimize any possible influence caused by fluctuations in the atmospheric pressure.

The results of this test II is shown in Table III and FIG. 4. Further, in comparison, a similar test was conducted using the same corn salad oil with addition of 0.02% by weight of BHA or without addition of any anti-oxidant. The results are given in Table III.

Table III

| Anti-oxidant | Oxygen absorption, $\mu$l/g Time, hours | | | | | | | |
|---|---|---|---|---|---|---|---|---|
| | 85 | 140 | 166 | 199 | 263 | 288 | 320 | 343 |
| Inventive compound | 84.4 | 138.7 | 159.8 | 174.8 | 238.0 | 280.4 | 334.6 | 375.3 |
| BHA | 57.6 | 116.2 | 174.8 | 219.0 | 478.9 | 697.8 | 922.9 | 1124.2 |
| None | 52.9 | 94.1 | 152.9 | 199.9 | 517.5 | 729.2 | 964.9 | 1164.3 |

What is claimed is:

1. A method for preventing oxidation of a foodstuff comprising admixing pure 2',6'-dihydroxy-9-(2,5-dihydroxyphenyl)-octylphenone in the foodstuff in an amount effective to prevent the oxidation of the foodstuff.

2. A composition comprising a foodstuff and pure 2',6'-dihydroxy-9-(2,5-dihydroxyphenyl)octylphenone in an amount effective to prevent oxidation of the foodstuff.

3. The method of claim 1 wherein the amount of the 2',6'-dihydroxy-9-(2,5-dihydroxyphenyl)-octylphenone is in the range from about 0.001 to 0.1 percent by weight based on the weight of the foodstuff.

* * * * *

Table II

| Anti-oxidant added, % by weight | Time, hours | | | | | | | | | | | | Peroxide value, meq./kg | | | | | |
|---|---|---|---|---|---|---|---|---|---|---|---|---|---|---|---|---|---|---|
| | 8 | 16 | 24 | 32 | 40 | 48 | 56 | 64 | 72 | 80 | 96 | 112 | 120 | 144 | 168 | 192 | 200 | 264 |
| Inventive compound, 0.1% | 2.1 | 3.0 | 4.1 | 5.2 | 7.9 | 8.7 | 9.9 | 11.8 | 13.5 | 16.0 | 18.5 | 24.0 | 24.1 | 29.9 | 32.1 | 38.1 | 45.0 | 678.2 |
| Inventive compound, 0.02% | 1.8 | 2.9 | 3.8 | 4.5 | 6.0 | 7.2 | 8.2 | 10.6 | 13.2 | 14.5 | 21.5 | 59.3 | 390.7 | — | — | — | — | — |
| Inventive compound, 0.01% | 1.5 | 3.2 | 4.8 | 5.4 | 7.7 | 9.3 | 11.3 | 15.4 | 22.1 | 170.9 | — | — | — | — | — | — | — | — |
| Inventive compound, 0.005% | 1.8 | 5.0 | 5.9 | 6.3 | — | 12.0 | 18.2 | 560.9 | — | — | — | — | — | — | — | — | — | — |
| Inventive compound, 0.001 | 2.4 | 5.3 | 8.2 | 14.9 | 419.9 | — | — | — | — | — | — | — | — | — | — | — | — | — |
| BHA, 0.02% | 2.8 | 5.1 | 7.9 | 13.8 | 28.9 | 33.1 | 43.1 | 97.3 | 296.7 | — | — | — | — | — | — | — | — | — |
| None | 4.7 | 5.5 | 10.3 | 28.5 | 425.1 | — | — | — | — | — | — | — | — | — | — | — | — | — |